Figure 1:
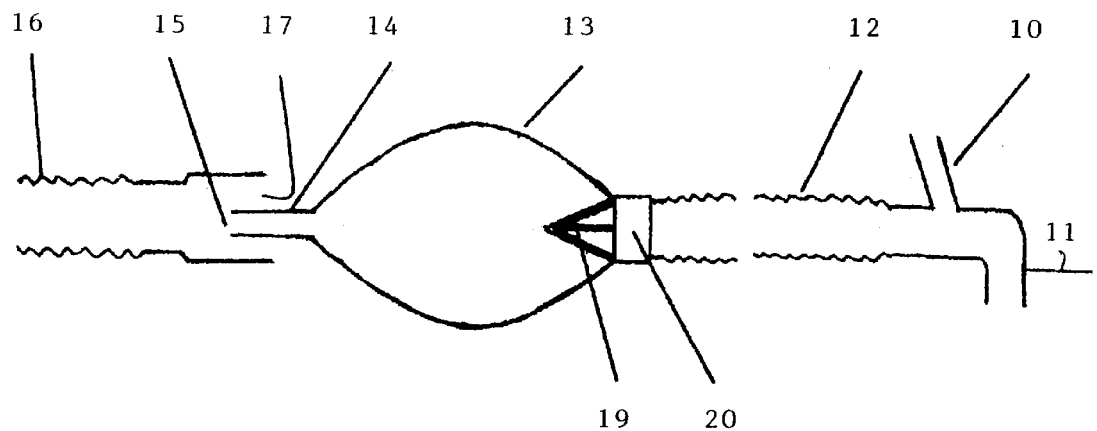

United States Patent

Aglan

[11] Patent Number: 6,041,781
[45] Date of Patent: Mar. 28, 2000

[54] BREATHING BAG

[76] Inventor: Magdy Yassin Aglan, 1 Byre Close Sale, Manchester, M33 2LY, United Kingdom

[21] Appl. No.: 08/854,885

[22] Filed: May 12, 1997

[30] Foreign Application Priority Data

May 14, 1996 [GB] United Kingdom .................. 9610060

[51] Int. Cl.[7] ........................................ A62B 7/00
[52] U.S. Cl. ................................ 128/205.17; 128/205.19
[58] Field of Search ........................ 128/203.28, 204.28, 128/205.13, 205.17, 205.19, 910

[56] References Cited

U.S. PATENT DOCUMENTS

| | | | |
|---|---|---|---|
| 3,662,774 | 5/1972 | Johannisson et al. | 128/910 |
| 3,901,230 | 8/1975 | Henkin | 128/910 |
| 4,029,093 | 6/1977 | Kohnke | 128/203.28 |
| 4,109,651 | 8/1978 | Steigerwald | 128/910 |
| 4,112,940 | 9/1978 | Parkes | 128/910 |
| 4,265,239 | 5/1981 | Fischer, Jr. et al. | 128/910 |
| 4,320,754 | 3/1982 | Watson et al. | 128/205.13 |
| 4,596,246 | 6/1986 | Lyall | 128/203.28 |
| 5,427,091 | 6/1995 | Phillips | 128/205.13 |

FOREIGN PATENT DOCUMENTS 2174607 11/1986 United Kingdom .................. 128/910

*Primary Examiner*—Aaron J. Lewis
*Attorney, Agent, or Firm*—Bergert & Bergert

[57] ABSTRACT

A breathing bag for inclusion in an open-circuit respirating system in which anaesthetic gases are supplied from an inlet duct (10) to a mask connected at (11). The bag (13) is connected at one end to a flexible exhalation duct (12), and has an open tail (14) as an escape passageway at the other end. An internal rod (21) connects the bag (13) pivotally to a ball and socket joint (22, 23) mounted on a rigid sleeve (25) adapted for connection to a scavenging system. A flexible bellows (27) adjustably surrounds the tail (14) thus to enable ready connection and disconnection of the rod (21) and sleeve (25) while being extendible to minimise or prevent the escape (at 17) of anaesthetic gases to the atmosphere.

10 Claims, 1 Drawing Sheet

BREATHING BAG

This invention concerns open-circuit respirating systems of the kind employed in administering anaesthetic gases to patients and particularly, though not exclusively, to paediatric patients.

Conventionally, for paediatric use an open-circuit anaesthesia delivery system comprises a duct with mask which is placed over the patient's nose and mouth and to which anaesthetic gases may be supplied under controlled volume and pressure. Exhaled gases are passed along the duct in the reverse direction and vented from a distal part of the circuit through a compressible double-ended breathing bag. One end of the bag is attached to the circuit and the other end has an open tail or escape passageway where excess anaesthetic gases escape to atmosphere. There is no valve at the escape passageway ensuring that little or no effort is required by the patient to exhale in the normal breathing cycle.

Such an open circuit system is utilised for children or infirm patients who may not have sufficient respiratory strength to receive anaesthesia in a closed circuit system incorporating valves and other mechanical devices which can be operated in the respiratory cycle of an adult or stronger person. The main problem with such an open circuit system is pollution of the atmosphere with anaesthetic gases because scavenging is difficult and inconsistent.

Many proposals have been tried including the addition of a value in the tail of the bag, but this increased the resistance to breathing.

In an operating theatre an anaesthetist must maintain manual control over the breathing bag in order to assist the breathing cycle when necessary, and to scavenge from this open-circuit system, requires that the escape passageway, or the tail of the bag, shall be located within an open end of a duct leading to the scavenging system. This can kink the tail of the bag with the resulting serious increase in the airway pressure. Also, since the parts are not rigidly connected together it is sometimes difficult for the anaesthetist to manipulate them whilst ensuring that the patient is breathing properly and that there is minimal escape of exhaled or fresh anaesthetic gases into the surrounding atmosphere.

According to the present invention a breathing bag adapted for inclusion in an open-circuit respirating system, comprises an escape passageway in the bag, a first link member attached or adapted to be attached to the bag, a second link member spaced from the bag and attached or adapted to be attached to the first link member, and means attached to the second link member and adjustable to control the escape of gases through the passageway.

Preferably, the first and second link members are connectable one to the other in a pivotable manner to assist manipulation of the breathing bag angularly with respect to a duct leading to a scavenging system.

Still further, the first link member preferably extends longitudinally and centrally within the bag passing axially and outwardly through a tubular tail forming the escape passageway, the second link member forming a sleeve having on end open and the other end attachable to a scavenging system, the open end of the sleeve having attached thereto a collapsible bellows extendible selectively over the tubular tail.

Figure 2:
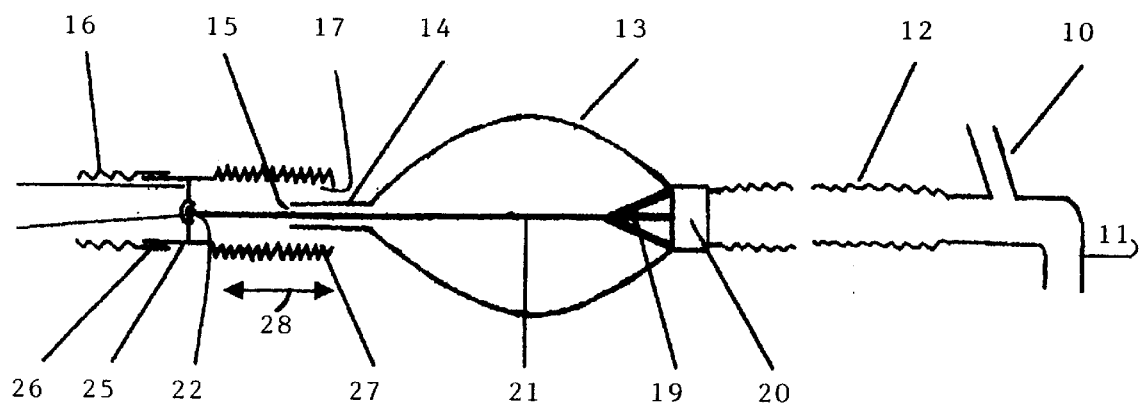

An embodiment of the invention will now be described, by way of example only, with reference to the accompanying drawings, in which:

FIG. 1 is a schematic representation of a conventional open-circuit respiratory and anaesthesia delivery system; and FIG. 2 is a view similar to FIG. 1 of such a system made in accordance with the invention.

Referring now to FIG. 1, in a simple open-circuit system anaesthetic gases are delivered under controlled volume and pressure to an inlet duct 10 having an extension 11 leading to a mask (not shown) which may be applied over the patient's mouth and nose.

The duct 10 is usually of a pre-formed rigid or semi-rigid material and the extension 11 is adapted to be connected to a flexible exhalation duct 12 which in turn is connected to the interior of a rubber breathing bag 13 by way of a rigid sleeve 20 having a skeletal frame 19. The duct 12 and bag 13 are attached with a friction fit to the sleeve 20. At an outlet end of the bag 13 there is a tubular tail 14 defining an escape passageway 15 through which exhaled gases may escape into a further duct 16 connected to a scavenging system. It will be seen that the system is open to air at 17 so that the patient is not required to exhale through any restriction such as a one-way valve. An anaesthesia delivery system of the kind described is often used for paediatric or elderly or infirm patients as there is minimal resistance to spontaneous breathing.

However, the anaesthetist must maintain the tail 14 within the open end of duct 16 whilst preventing obstruction of the passageway at 14, 15 and 17. Apart from the difficulty in holding the parts in close but open relationship while administering anaesthesia and controlling the patient's breathing if appropriate by depressing the bag 13, there is also a risk that exhaled or fresh anaesthetic gases, or a mixture of both, can leak back into the surrounding atmosphere through the opening 17 thus contaminating the atmosphere and placing the anaesthetist, surgeon and theatre staff at risk.

Referring not to FIG. 2, and in accordance with the invention, a nylon or other plastics rod 21 is fixed to the skeletal frame 10 and extends longitudinally and centrally through the bag 13 and tail 14 to emerge beyond the passage 15. At the remote end of the rod 21 is a ball 22 forming part of a pivotal ball and socket joint the other part 23 of which is connected by spokes 24 to the internal wall of a sleeve 25 to which the free end 26 of the duct 16 (the standard scavenging tubing) may be attached. To the opposite end of sleeve 25 there is attached a bellows 27 which may extend in the direction of arrows 28 partially to occlude the opening 17. In use, initially, the bellows 27 may be compressed to allow easy connection of the ball 22 to socket 23. Then the bellows are extended to overlie part of the tail 14 and thus restrict the annular escape passageway therearound.

It will be appreciated that the degree to which the bellows 27 are extended is selectable thus to allow adequate manual control of the bag 13 and maintain the air passage 17 while minimising or preventing the escape of anaesthetic gases therethrough, and the universally pivotable connection of the ball and socket joint 22, 23 maintains a connection between the breathing bag 13 and the scavenging duct 16 whereby the anaesthetist need not manually maintain these two parts in position. Once the bellows 27 are set this part of the respiratory system need not be further manipulated until it is required to disconnect the parts one from another by retracting the bellows 27 and separating the ball and socket joints 22, 23. Thus the anaesthetist is left free to manipulate the bag 13 as necessary pinching the tail 14 as required to assist the patient's breathing.

The tail 14 shall have an optimal length to facilitate scavenging while allowing adequate manual control of the bag.

This system provides a simple, effective, reliable, flexible and much safer connection between the breathing circuit and the scavenging system. It enables the patient to breath gently and evenly without a valve or obstruction while presenting the escape of potentially hazardous anaesthetic gases continuously during spontaneous and manually assisted ventilation. It maintains an open circuit so that the vacuum line does not act on the patient's anaesthetic circuit. Also, the rod 21 helps to prevent kinking of the tail 14 of the bag.

It is not intended to limit the invention to the above example only. For example, a different form of connection of the bag 13 to the sleeve 25 may be provided, and the link member 21 may be located outside of and spaced from the bag 13 and connectable, preferably pivotally, with a swivel connection which is easily coupled to and decoupled from the sleeve 25 whilst allowing manipulation of the walls of the bag. Also, the bellows 27 may be replaced by telescopically extending tubular members. Furthermore, the rod 21 may be fixed to the sleeve 25 and removably attachable to the sleeve 20, thus being readily adaptable to other breathing circuits.

I claim:

1. A breathing bag adapted for inclusion in an open-circuit respirating system, having an interior and inlet and outlet parts, the inlet part being attachable to a duct to receive exhaled gases therefrom, and the outlet part comprising an open conduit communicating with the interior of the bag for flow of gases out of the bag, the open conduit to be inserted freely within an open-ended gas scavenging duct thereby leaving a selectively varying size passage open to atmosphere between an outer surface of the open conduit and an inner surface of such an open-ended scavenging duct; said breathing bag further having a first link member attached thereto, a second link member spaced from the bag and attached or attachable to the scavenging duct and to the first link member, and means attached to the second link member for selectively adjusting the size of such a passage.

2. A breathing bag according to claim 1, wherein the first and second link members are connectable one to the other in a pivotable manner to assist manipulation of the breathing bag angularly with respect to the scavenging duct.

3. A breathing bag according to claim 2, wherein the first and second link members form between them a pivotal ball and socket joint.

4. A breathing bag according to claim 1, wherein the open conduit is tubular, the first link member extends longitudinally and centrally within the bag passing axially and outwardly through the open tubular conduit, the second link member being a sleeve having an open end, and the selectively adjusting means being a collapsible bellows attached to said open end.

5. A breathing bag according to claim 4, in which the first link member is a rod attached internally to the bad adjacent the inlet part thereof and extending through the interior thereof to emerge from the open tubular conduit and having a ball on a remote end thereof, the second link member forming a rigid sleeve with a socket connected by spokes to an internal wall of the sleeve and adapted removably to engage said ball.

6. A breathing bag according to claim 5, further comprising a skeletal frame within the breathing bag, the rod being attached to the skeletal frame.

7. A breathing bag according to claim 4, wherein the collapsible bellows overlies the open tubular conduit of the bag and is extendible longitudinally with respect to the open tubular conduit so as adjustably to restrict an annular passageway between an inner surface of the bellows and an outer surface of the open tubular conduit.

8. A breathing bag according to claim 1, wherein the selectively adjusting means is a plurality of telescopically extending tubular members.

9. A breathing bag according to claim 1, wherein the first link member is fixed to the second link member and is removably attached to an end of the bag remote from the open tubular conduit.

10. A breathing bag according to claim 1, wherein the first link member is located outside of and spaced from the bag and connectable pivotally to the second link member being readily coupled to and decoupled from a scavenging system.

* * * * *